United States Patent [19]
Cherqui et al.

[11] 4,264,574
[45] Apr. 28, 1981

[54] NEW GALENICAL FORM OF ADMINISTRATION OF BETAHISTINE AND ITS DERIVATIVES AND THE PREPARATION THEREOF

[76] Inventors: Jean S. Cherqui, 55, rue Pergolèse, 75016 Paris; Alain C. Djiane, 105 Avenue du Roule, 92200 Neuilly-sur-Seine, both of France

[21] Appl. No.: 122,617

[22] Filed: Feb. 19, 1980

Related U.S. Application Data

[63] Continuation-in-part of Ser. No. 27,351, Jun. 5, 1979.

[30] Foreign Application Priority Data

Jul. 22, 1977 [FR] France .................. 77 22495

[51] Int. Cl.³ .................. A61K 9/22; A61K 9/24; A61K 9/26; A61K 9/52

[52] U.S. Cl. .................. 424/19; 424/20; 424/21; 424/22

[58] Field of Search .................. 424/19-22

[56] References Cited

U.S. PATENT DOCUMENTS 3,410,861  8/1965  McCloskey .................. 260/296
4,229,428 10/1980  Chorqui et al. .................. 424/19

FOREIGN PATENT DOCUMENTS 2397840  2/1979  France .

Primary Examiner—Shep K. Rose
Attorney, Agent, or Firm—Omri M. Behr

[57] ABSTRACT

A new galenical form of administration of betahistine and its derivatives, its preparation method and pharmaceutical products containing this new galenical form.

9 Claims, No Drawings

NEW GALENICAL FORM OF ADMINISTRATION OF BETAHISTINE AND ITS DERIVATIVES AND THE PREPARATION THEREOF

This application is a continuation in part application of our previous application Ser. No. 027,351 filed on Apr. 5, 1979.

The object of the present invention is to treat the buzzing in the ears and the vertigo of Meniere's syndrome with this new pharmaceutical form.

The invention consists of a pharmaceutical form containing a salt of 2-(methylaminoethyl) pyridine contained in microspheres.

This new pharmaceutical form is a long acting medication which is better tolerated.

PREFERRED EMBODIMENTS OF THE INVENTION

The object of the present invention is to treat the buzzing of the ears and the vertigo of Meniere's syndrome with this new pharmaceutical product.

It is known that this type of symptom appears mostly in the elderly patient, that long term treatment is necessary and that perfect tolerance of the product is therefore required.

Until now, the principle product used in the treatment of these problems is 2-methylaminoethyl pyridine hydrochloride, also called betahistine hydrochloride. However, this product, although very valuable therapeutically, has had limited success on the market because of the precautions necessary during its usage and because of the side effects occuring during treatment. Also, the short action of this substance necessitates frequent doses. In fact, the daily dosage can be as much as 48 mg, taken in 6 dividided doses.

It is known that betahistine has a histamine-like action on the secretory cells of the gastric mucosa and that its use is inadvisable in patients with gastric ulcers, or suffering from gastric hyperchlorhydria.

It was thus advantageous to be able to have at our disposal a new pharmaceutical form which assures regular and prolonged diffusion of the active ingredient while eliminating the risks of intolerance.

The pharmaceutical forms according to the invention avoid the previously mentioned inconveniences and place at the disposal of the doctor a new therapeutic agent which has a safety level and weak enough dose to allow long term treatment.

The pharmaceutical forms according to the invention are characterised by the presence of betahistine methanesulphonate contained in microcapsules which are in turn contained in small spheres with semi-permeable membranes. This pharmaceutical form releases betahistine progressively as the pH of the digestive juices increases.

According to the invention the semi-permeable membrane consists of successive concentric layers of a material selected from the group consisting of methacrylic polymers and shellac and the thickness of the membrane determines the rate of release of the active ingredient. The active ingredient is incorporated in these microgranules in the form of a dispersion in an inert substance and is dispersed in the methacrylic mass or solutions of this polymer in a volatile solvent, or in a solution of shellac in a volatile solvent.

To cite examples, the inert substances can be starch, talc, lactose, saccharose, colloidal silica, celluloses, stearic acid or magnesium stearate, magnesium phosphate or alumina or a mixture of two or several of these inert substances.

The methacrylic polymer is preferably that sold under the brand name of EUDRAGIT.

The shellac is preferably that sold under the brand name of DIFFULAC.

The pharmaceutical forms according to the invention are presented in the form of transparent or opaque capsules containing a fixed number of microgranules or in the form of flavoured or unflavoured suspensions.

On contact with the digestive juices in the stomach, the capsules open and release a large number of these microgranules which thus convert a single dose into a large number of autonomic sub-doses. This multiplication allows a greater dispersion and thus a satisfactory absorption and a prolonged action.

The capsules according to the invention contain 5 to 25 mg, and preferably 12 mg, of the active ingredient.

The daily dose is 30 to 40 mg of the active ingredient and is provided by 2 to 3 capsules, preferably 3. It can thus be seen that the composition of the invention allows treatment of the vertigo of Meniere's disease with a dose which is reduced by 50% and prevents, to the highest possible degree, undesirable side-effects. The duration of treatment is from 6 weeks to 6 months according to the therapeutic indications.

The compositions according to the invention were tested in the treatment of the buzzing in the ears and vertigo in Meniere's syndrome and Meniere's disease and also in the treatment of cerebral circulatory insufficiency. These treatments are particularly intended for the elderly patient (70 years or over) but younger patients were nevertheless treated under identical conditions.

Example of the manufacture of a pharmaceutical form according to the invention

A starting granule of a mixture of starch, saccharose and stearic acid is made. The sifted granules are then placed in a stainless steel turbine which has sufficient speed and rotating time to obtain perfectly spherical grains. A second sieving is carried out, then the granules are dried.

The granules thus obtained are perfectly calibrated and ready to receive applications of several layers of the active ingredient and various coating layers.

A certain quantity of these microgranules is placed in the turbine then slightly wetted with a concentrated saccharose solution. Whilst the microgranules are still damp, a solution of BETAHISTINE methane sulphonate in 95° ethanol is slowly sprayed over the surface of the microgranules. Rotation is continued until the entire amount of the active ingredient required for the layer has been deposited. The microgranules are then dried in a ventilated dryer.

Once this operation is completed, an alcoholic solution of metacrylic polymers or shellac is sprayed onto the microgranules.

These two last-mentioned operations (distributing of the active ingredient and successive coatings) are repeated several times. The successive layers of coating contain from the outside towards the inside of the microgranules, concentrations or increasingly thick layers of shellac or of methacrylic polymers.

Thus, for example, for 4 sucessive coatings, the concentration in the various layers can vary from 5 to 35% of the total quantity of shellac to be used, as follows:

1st internal layer: 35% of the total quantity of shellac
2nd internal layer: 25% of the total quantity of shellac
3rd intermediate layer: 25% of the total quantity of shellac
4th external layer: 5% of the total quantity of shellac.

Once these operations are completed, the microgranules are dried for 2 to 4 days in a ventilated drying cupboard at room temperature.

In the next step, the determination of the active microgranules is carried out and the necesssary quantity of inactive non-coated microgranules is added until a mixture containing the required quantity of betahistine is obtained. The microgranules are then put into capsules, each capsule preferably containing 240 mg of microgranules.

Example of manufacture of 100,000 capsules, each capsule containing 12 mg of the active ingredient.

| active microgranules | |
|---|---|
| Betahistine methanesulphonate | 1.200 kg |
| Saccharose | 8.160 kg |
| Cornstarch | 2.730 kg |
| Stearic acid | 0.010 kg |
| Diffulac | 1.160 kg |
| Talc | 2.950 kg |
| Colloidal Silica | 1.300 kg |
|  | 17.510 kg |
| Adjuncts to the manufacturing process: | |
| Ethanol 95° | q.s. |
| Distilled water, acetone | q.s. |
| inactive microgranules | |
| Saccharose | 5.060 kg |
| Cornstarch | 1.420 kg |
| Stearic acid | 0.010 kg |

Assay of the rate of release of betahistine methanesulphonate

The rate of release of betahistine methanesulphonate is within the following limits:

|  | Percentage released | limits |
|---|---|---|
| 1st hour | 31.1% | less than 40% |
| 4th hour | 68.5% | 40 to 80% |
| 8th hour | 90.7% | more than 80% |

These controls were carried out under controlled conditions, using the appropriate equipment, to reproduce conditions encountered in the body.

Thus, the release during the first hour is tested in artificial gastric medium with a pH of 1.5 and after 1 hour the medium is changed and the microgranules are placed in artificial intestinal medium at a pH of 7.2.

The equipment used allows constant stirring and maintenance of a constant temperature of between 36.5° and 37.5° C.

Each manufacturing batch of microgranules can be tested in this manner and the coating modified accordingly.

Report of Clinical Trials

These clinical trials above all consisted of clinical pharmacological studies in man and the aim of these investigations was to verify the prolonged action of betahistine methanesulphonate in the pharmaceutical form according to the invention.

Pharmacological Investigations

The method used consisted of the measuring of the resistance index using ultrasonic velocimetry (Doppler effect) employing a Doppler SV 30 IERAM machine.

The Doppler curves were recorded hourly for 8 hours and were taken from the carotid arteries in a statistically significant number of patients. Amongst the objective measurements, the vascular resistance index was taken into account and is in fact obtained from the relationship between the increase in systolic flow rate and maximal systolic flow rate. A decrease in this index favours a vasodilatation and vica versa.

The results obtained are as follows:

| | | | | | Time | | | | |
|---|---|---|---|---|---|---|---|---|---|
| R Index | To | 1h | 2h | 3h | 4h | 5h | 6h | 7h | 8h |
| IR | 0.875 | 0.86 | 0.80 | 0.80 | 0.77 | 0.82 | 0.80 | 0.83 | 0.87 |
|  | ±0.04 | ±0.03 | ±0.10 | ±0.07 | ±0.10 | ±0.07 | ±0.08 | ±0.07 | ±0.05 |
| P |  | NS | <0.02 | 0.0001 | <0.05 | <0.01 | <0.05 | <0.01 | <NS |

IR = Vascular Resistance Index

These results show that from the 2nd hour until the 7th hour, betahistine methanesulphonate administered in the pharmaceutical form according to the invention possesses statistically significative vasodilatatory activity.

Report of Clinical Trials

A—Cerebral circulatory insufficiency problems

The clinical trials were conducted in 40 patients. The trial was a double blind with a placebo serving as reference product.

The duration of treatment was 12 weeks, divided into two periods of 6 weeks with a 2-week wash-out period in between. The wash-out period was necessary to ensure that there were no remaining effects from the preceding treatment.

The order of administration of the treatments was determined at random and the code provided by the manufacturer was kept in a sealed envelope to be opened only at the completion of the trial.

The distribution of the medications and their administration was regulated using standard protocol throughout the duration of the trial. The standardisation of nursing procedures, to which we attached great importance in the evolution of a therapy destined to improve cerebral circulation in senescent patients, was rigorously observed.

The psychometric tests designed to evaluate the CRICHTON rating scale were performed in the same department, following particularly thoroughly tested methods.

RESULTS

1st evaluation

The results obtained were evaluated in both clinical and psychological terms. This evaluation was facilitated by the use of the quantitative Crichton rating scale. The systematic study of these various parameters allowed the demonstration of the most improved criteria after each treatment.

We classed the results as: Good, Medium or Failure, being based on both the clinical state of the patient and on the number of items improved.

GOOD

The whole group of items improved

MEDIUM

An improvement, indicated by the different parameters, from subjective and objective points of view.

FAILURE

Persistent debility (physical and psychological) reflected in a lack of change in the tests, negative to begin with, and an unchanged clinical status.

(2°) Tolerance (a) Biological tolerance-

We used the normal tests for verifying the tolerance, bearing in mind the known characteristics of betahistine. The following tests were performed before and after the treatments:

urea
glucose
cholesterol
transaminase SGOT/SGPT
haemoglobin
blood count (b) Clinical tolerance We considered cardiovascular surveillance to be of utmost importance. We performed the following tests:
arterial blood pressure before, during and after treatment.
cardiac rhythm before, during and after treatment
ECG before and after treatment.

Gastrointestinal surveillance, intestinal transit time, nausea, vomiting and neurological surveillance were performed by the nursing staff as well as the observations followed in the tests for measuring the effectiveness of the product.

RESULTS

The treatment was divided into 2 periods of 6 weeks. The results obtained are as follows:

| 1st group: Series Placebo-Active product | | |
|---|---|---|
| . Placebo | 5 medium results, | being 25% |
|  | 15 failures | being 75% |
| . Active product | 16 good results, | being 80% |
|  | 3 medium results, | being 15% |
|  | 1 failure | being 5% |
| 2nd group: Series Active product - placebo | | |
| . Active product | 12 good results, | being 60% |
|  | 4 medium results, | being 20% |
|  | 4 failures | being 20% |
| . Placebo | 20 failures | being 100% |

These results show a net improvement under treatment with the active product, being:

| . 28 good results, | being 70% |
|---|---|
| . 7 medium results, | being 17.5% |
| . 5 failures, | being 12.5% |

ANALYSIS OF RESULTS 40 patients were treated in this controlled clinical trial which was a double blind crossover with a placebo as reference product. The advantage of a trial of this nature is that only a limited number of subjects is necessary. There were:

11 male patients, representing 27.5% of the total
29 female patients, representing 72.5% of the total.
The number of patients corresponds to the number generally used in this type of trial in geriatric patients.

Several remarks can be made at the end of this trial:
no patient stopped his treatment during the trial
we observed no side effects.

The tolerance was in general good except for a few cases of mild tolerance.

The symptoms improved the most by treatment with the invention were:

| Series placebo-active product: | |
|---|---|
| anxiety, fear | 77% |
| emotional stability | 73.7% |
| liveliness, confusion | 68.5% |
| reactional depression | 64.3% |
| vertigo | 61.5% |
| appetite | 61.5% |
| headaches | 54.55% |
| sleep | 53% |
| buzzing in the ears | 50% |
| Series active product-placebo: | |
| anxiety, fear | 86.7% |
| fatigue | 83.4% |
| emotional stability | 73.3% |
| liveliness, confusion | 69.2% |
| reactional depression | 62.5% |
| headaches | 62.5% |
| orientation | 57% |
| vertigo | 50% |

These results show that betahistine has, without any doubt, a positive effect on cerebral circulation. The results show in particular a marked improvement in the physiological status of the patients. The very significant improvement in certain items, such as vertigo, fatigue, headaches, sleep, buzzing in the ears, confirms the clinical effectiveness of the product in treating cerebral circulatory insufficiency.

(c) Biological tolerance

The biological tolerance was excellent in all cases. There were:
no modifications in blood count
no variations in urea or glucose levels
no change in hepatic function.

(B)-Treatment of Meniere's disease (a) Open clinical trial:

The trial was conducted in 25 patients with an average age of 42.5 years. There were 10 men and 15 women. Patients selected were all patients presenting with a Meniere's syndrome of 6 months to 20 years since the onset.

The dosage and the therapeutic plan were established taking into account the level at which betahistine is active and at the same time the particular galenical form of the compositions according to the invention.

Betahistine was administered at a dosage level of 3 capsules per day, each capsule containing 12 mg of betahistine methanesulphonate.

The length of treatment was fixed at a minimum of 3 months. The treatment period was extended to 6 or even 9 months in certain cases.

Criteria for evaluating effectiveness:
Meniere's disease in its acute phase is characterised by 3 distinct symptoms:
vertigo
buzzing in the ears
deafness.

Vertigo is a symptom apart, in which the patient has the sensation that surrounding objects are rotating.

The acute phase may last several hours and may be accompanied by spectacular neurovegetative signs.

The estimation of the clinical effectiveness of the product was based on such objective criteria. Before and after each treatment, labyrinthic tests, an audiogram were performed, then the following clinical signs were evaluated: vertigo, nausea, otalgia, headaches, tinnitus aurium.

Analysis of results

Independent of the clinical evaluation, it seemed necessary to divide the previously cited clinical parameters into: very good, good, quite good, medium, and failure.

At the same time, special importance was attached to gastrointestinal surveillance as well as to cardiovascular and neurological tolerance for the composition according to the invention.

Conclusions

At the end of the trial, it was seen that no patient interrupted treatment, and that there were no side effects and that the tolerance was overall very good for the compositions.

The trial was conducted in 25 patients, and the following results were obtained:
very good and good results = 16 cases, being 64%
quite good and medium = 6 cases, being 24%
failure = 3 cases, being 12%

The results obtained thus show that the compositions according to the invention exert a very marked therapeutic activity and that the compositions are very active in the treatment of Meniere's syndrome and also that long term administration does not call for any particular caution.

Among the symptoms used as objective criteria, it is important to note that vertigo was improved in 88% of cases, nausea in 91% of cases and otalgia in all cases.

On the average, the delay of action of the product is 10 days; the duration of action lasts throughout treatment.

The pharmaceutical compositions according to the invention were, from patient's remarks, much better tolerated than the non long-acting tablet form.

The biological tolerance was excellent in all cases.

(b) Double blind clinical trial:

This trial was a double blind cross-over trial comparing betahistine hydrochloride in 8 mg tablet form with betahistine methanesulphonate in the pharmaceutical form according to the invention and it was conducted primarily in patients presenting with Meniere's disease and tinnitus.

The daily dose for each patient (decoded on completion of treatment) was:
3 capsules of long-acting betahistine methanesulphonate the equivalent of 5 to 6 8 mg tablets of betahistine hydrochloride.

The total duration of each treatment was at least 12 weeks and the criteria used to evaluate efficacity were the same as those used previously, that is: clinical signs, ENT examinations and measurement of clinical and biological tolerance.

In the 16 patients who completed the trial, the results were as follows:

| Medication | Clinical results | | | Gastric intolerance | |
|---|---|---|---|---|---|
| | satisfactory | doubtful | failure | severe | mild |
| betahistine hydrochloride | 5 | 5 | 6 | 10 | 2 |
| betahistine methanesulphonate | 15 | 0 | 1 | 0 | 0 |

This study designed to demonstrate the effectiveness/tolerance of BETAHISTINE methanesulphonate in a long-acting form according to the invention compared with another marketed form of betahistine, 8 mg tablets of betahistine hydrochloride, showed that long-acting BETAHISTINE has a statistically significantly more marked action with an $\alpha$ risk of between 0.01 and 0.001 for effectiveness and an $\alpha$ risk greater than 0.001 for tolerance.

It would thus seem that betahistine is a very active substance, and this activity is enhanced by the excellent degree of tolerance on the part of the patients, which is not the case in other pharmaceutical administration forms, particularly 8 mg tablets of betahistine hydrochloride.

This new pharmaceutical administration form which progressively releases the active ingredient leads to the disappearance of side effects, increased efficacy and above all to a reduction in the dose necessary in the treatment of Meniere's disease which is of necessity a long term treatment.

In this trial, it should be noted that the optimum quantities of betahistine prescribed were the equivalent of:
3 capsules of long-acting betahistine methanesulphonate, i.e. 4.9 mg of betahistine base per capsule
5 8 mg tablets of betahistine hydrochloride, i.e. 5.2 mg of betahistine base per tablet
which represents a total effective daily dose of betahistine base of:
14.7 mg for long-acting betahistine methanesulphonate, or
26 mg for betahistine hydrochloride.

This reduction of almost 50% in the dose of betahistine when administered in the form of the pharmaceutical administration form according to the invention constitutes a considerably improved therapy.

What we claim is:

1. A therapeutically useful and pharmacologically acceptable oral depot medicament in the form of substantially uniformly sized spheroidal particles containing 2-methylaminoethyl pyridinemethanesulphonate as the active ingredient thereof comprising
   (a) an inactive core of pharmaceutically acceptable carrier material;
   (b) at least two sets of sequential bipartite layers on said core comprising an inner layer of the active ingredient and an outer layer of a dialysis membrane, said membrane being substantially insoluble in neutral or acid environments but soluble above pH 7.

2. A medicament in accordance with claim 1 wherein the inner layer of said sequential bipartite layer outwardly of the first dialysis membrane outwardly of the inactive core, additionally comprises pharmaceutically acceptable and pharmaceutically-inert carrier material upon which the active ingredient is adsorbed.

3. A medicament in accordance with claim 1 wherein said dialysis material is a material selected from the group consisting of an anionic polymerizate of methacrylic acid and methacrylic esters, and shellac.

4. A medicament in accordance with claim 3 wherein said medicament is further encapsulated in pharmaceutically acceptable capsules.

5. A method of treating vertigo in patients suffering from Meniere's syndrome which comprises administering to said patients an antivertigo effective amount of a composition of claim 1.

6. The method of claim 5 which comprises administering to said patients up to 48 mg per day of said active ingredient.

7. A method for treating Meniere's disease in patients suffering from said condition which consists in administering to said patients a safe but effective amount of the composition of claim 1.

8. The method of claim 7 in which the safe but effective amount of the composition of claim 1 incorporates from 30 to 40 mg of betahistine methanesulphonate per day.

9. A method for treating cerebrovascular deficiencies in patients suffering from said deficiency which consists in administering to said patients a safe but effective amount of a composition of claim 1.

* * * * *